United States Patent [19]
Gers-Barlag et al.

[11] Patent Number: 5,952,391
[45] Date of Patent: Sep. 14, 1999

[54] USE OF FLAVONES AND FLAVONOIDS AGAINST THE UV-INDUCED DECOMPOSITION OF DIBENZOYLMETHANE AND ITS DERIVATIVES

[75] Inventors: Heinrich Gers-Barlag, Kummerfeld; Oliver Scheel, Düsseldorf, both of Germany

[73] Assignee: Beiersdorf AG, Hamburg, Germany

[21] Appl. No.: 09/205,435

[22] Filed: Dec. 4, 1998

[30] Foreign Application Priority Data

Dec. 13, 1997 [DE] Germany ............... 197 55 504

[51] Int. Cl.⁶ ..................... A61K 31/12
[52] U.S. Cl. .............. 514/685; 424/59; 424/47; 203/78
[58] Field of Search ............ 514/685; 424/59, 424/47; 203/78

[56] References Cited

U.S. PATENT DOCUMENTS 5,034,213  7/1991  Rosenbaum et al. ............ 424/47
5,576,354  11/1996 Deflandre et al. ............ 514/685
5,837,107  11/1998 Watzenberger et al. ........ 203/78

FOREIGN PATENT DOCUMENTS 42 27 806  2/1993  Germany.
2259014  3/1993  United Kingdom.

*Primary Examiner*—Keith D. MacMillan
*Assistant Examiner*—Vizkie Kim
*Attorney, Agent, or Firm*—Sprung Kramer Schaefer & Briscoe

[57] ABSTRACT

Use of flavone derivatives and flavanone derivatives, in particular flavonoids for stabilizing cosmetic or dermatologically acceptable substances, the chemical formula of which includes the structural moiety of dibenzoylmethane, against the decomposition caused by UV radiation.

12 Claims, No Drawings

USE OF FLAVONES AND FLAVONOIDS AGAINST THE UV-INDUCED DECOMPOSITION OF DIBENZOYLMETHANE AND ITS DERIVATIVES

The present invention relates to cosmetic and dermatological light protection formulations, in particular skincare cosmetic and dermatological light protection formulations.

The damaging effect of the ultraviolet part of solar radiation on the skin is generally known. While rays having a wavelength of less than 290 nm (the UVC region) are absorbed by the ozone layer in the earth's atmosphere, rays in the region between 290 nm and 320 nm, the UVB region, cause erythema, simple sunburn or even burns of varying severity.

The narrower region around 308 nm is stated as the erythema activity maximum of sunlight.

Numerous compounds are known for protecting against UVB radiation; these are usually derivatives of 3-benzylidenecamphor, 4-aminobenzoic acid, cinnamic acid, salicylic acid, benzophenone and also 2-phenylbenzimidazole.

For the region between about 320 nm and about 400 nm, the UVA region, it is also important to have available filter substances, since the rays of that region can also cause damage. Thus, it has been found that UVA radiation leads to damage of the elastic and collagenic fibres of connective tissue, causing premature ageing of the skin, and that it is to be regarded as a cause of numerous phototoxic and photoallergic reactions. The damaging effect of UVB radiation can be intensified by UVA radiation.

UVA radiation can also cause skin damage by damaging the keratin or elastin present in the skin. As a result, elasticity and the ability of the skin to store water is reduced, i.e. the skin becomes less supple and tends towards wrinkling. The high incidence of skin cancer in regions where solar radiation is strong indicates that damage to the genetic information in the cells is also obviously caused by sunlight, in particular by UVA radiation.

However, UV radiation can also lead to photochemical reactions, in which case the photochemical reaction products intervene in the skin's metabolism.

Such photochemical reaction products are predominantly free-radical compounds, for example hydroxyl radicals. Undefined free-radical photo-products which are formed in the skin itself can also display uncontrolled secondary reactions because of their high reactivity. However, singlet oxygen, a non-radical excited state of the oxygen molecule, can also be formed during UV irradiation, as can short-lived epoxides and many others. Singlet oxygen, for example, differs from the normal triplet oxygen (free-radical ground state) by its increased reactivity. However, excited, reactive (free-radical) triplet states of the oxygen molecule also exist.

UV radiation is also a type of ionizing radiation. There is therefore the risk that UV exposure may also produce ionic species, which then, for their part, are capable of oxidative intervention in the biochemical processes.

A known and advantageous light protection filter substance is 4-(tert-butyl)-4'-methoxydibenzoylmethane, which is characterized by the structure

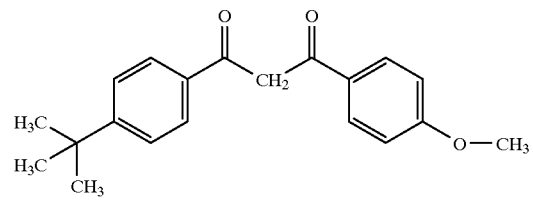

and is marketed by Givaudan under the trade name Parsol® 1789.

The main disadvantage of this substance is a certain instability towards UV radiation, making it expedient to also incorporate certain UV stabilizers into preparations containing this substance. The photochemical decomposition of 4-(tert-butyl)-4'-methoxydibenzoylmethane—as a representative for all dibenzoylmethane derivatives which absorb in the UV region—follows a Norrish type I acyl cleavage according to the following equation:

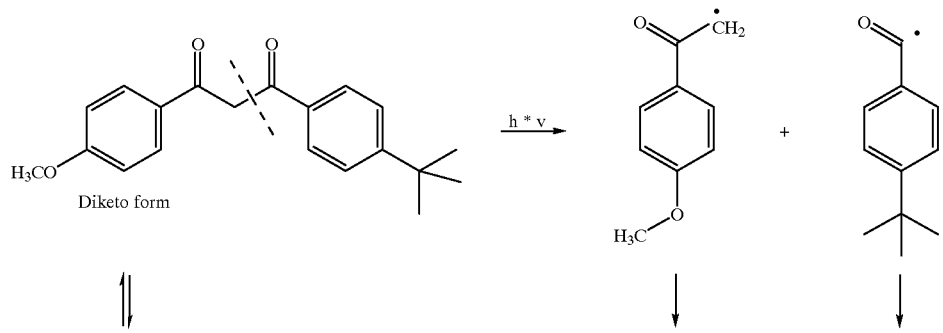

-continued

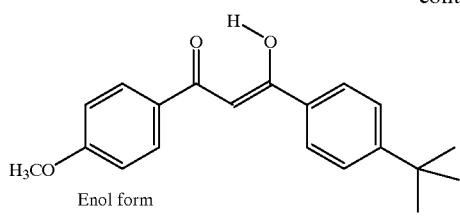
Enol form

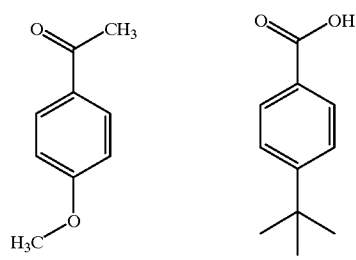

The reaction products are no longer available as light protection filter substances. There was thus an urgent need to find ways in which the photolytic decomposition of dibenzoylmethane derivatives can be effectively countered.

For example, German Laid-Open Specification DE-A-37 41 420 describes the combination of this light protection filter in a certain quantity ratio to 4-methylbenzylidenecamphor, which is characterized by the structure

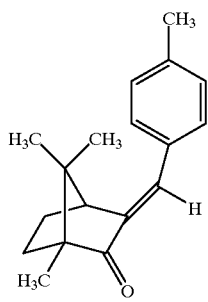

and is marketed by Merck under the trade name Eusolex® 6300. The preparations described loc. cit., however, are in turn characterized by other disadvantages, mainly one of a formulating nature.

To overcome the disadvantages of the prior art was thus the object of the present invention.

The use of flavones and flavonoids in cosmetics and dermatology is known per se. For example, DE-A 44 44 238 describes combinations of cinnamic acid derivatives and flavone glycosides, for example α-glycosylrutin as antioxidants and as active ingredients against other indications. The Laid-Open Patent Specifications JP-Heisei-08/099859, JP-Heisei-07/233046, JP-Heisei-06/321759 and EP-357042 describe the use of certain flavonoids as skin-whitening agents although this relates to the lightening of large areas of skin, which involves a different mechanism, namely the inhibition of tyrosinase activity or simply of UV absorption.

Flavone and its derivatives (often also collectively called "flavones") are characterized by the following basic structure (substitution positions are given):

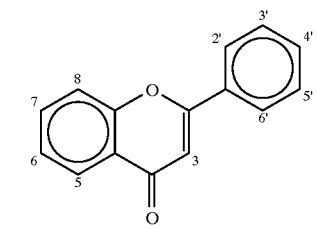

Some of the more important flavones, which can also be found in living nature, are given in the table below:

|  | OH substitution positions | | | | | | | |
| --- | --- | --- | --- | --- | --- | --- | --- | --- |
|  | 3 | 5 | 7 | 8 | 2' | 3' | 4' | 5' |
| Flavone | − | − | − | − | − | − | − | − |
| Flavonol | + | − | − | − | − | − | − | − |
| Chrysin | − | + | + | − | − | − | − | − |
| Galangin | + | + | + | − | − | − | − | − |
| Apigenin | − | + | + | − | − | − | + | − |
| Fisetin | + | − | + | − | − | + | + | − |
| Luteolin | − | + | + | − | − | + | + | − |
| Kaempferol | + | + | + | − | − | − | + | − |
| Quercetin | + | + | + | − | − | + | + | − |
| Morin | + | + | + | − | + | − | + | − |
| Robinetin | + | − | + | − | − | + | + | + |
| Gossypetin | + | + | + | + | − | + | + | − |
| Myricetin | + | + | + | − | − | + | + | + |

In nature, flavones are usually in glycosylated form.

It was therefore surprising and could not have been foreseen by the person skilled in the art that the use of cosmetically or pharmaceutically acceptable flavone derivatives and flavanone derivatives, in particular of flavonoids, for stabilizing cosmetic or dermatologically acceptable substances, the chemical formula of which includes the structural moiety of dibenzoylmethane,

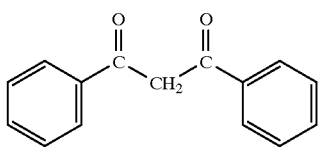

against the decomposition caused by UV radiation, overcomes the disadvantages of the prior art.

If flavone derivatives and flavanone derivatives, in particular, flavonoids, are present in cosmetic or dermatological preparations in combination with dibenzoylmethane derivatives, then the latter are protected against the decomposition caused by UV radiation in an excellent manner.

Flavonoids are glycosides of flavones, of flavanones, the basic skeleton of which is characterized by the following structure:

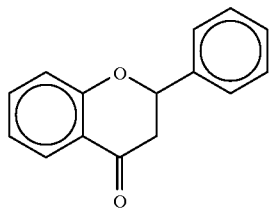

of 3-hydroxyflavones (flavonoles), the basic skeleton of which is characterized by the following structure:

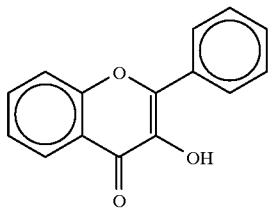

of aurones, the basic skeleton of which is characterized by the following structure:

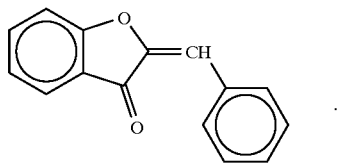

and also of isoflavones, the basic skeleton of which is characterized by the following structure:

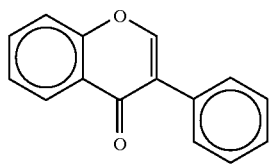

According to the invention, the flavonoids are preferably chosen from the group of substances having the generic structural formula

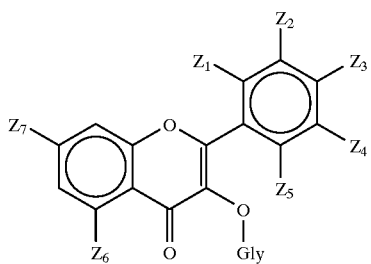

where $Z_1$–$Z_7$ independently of one another are chosen from the group consisting of H, OH, alkoxy and hydroxyalkoxy, where the alkoxy or hydroxyalkoxy groups may be branched or unbranched and may have 1–18 carbon atoms, and where Gly is chosen from the group of mono- and oligoglycoside radicals.

According to the invention, the flavonoids can however also be advantageously chosen from the group of substances having the generic structural formula

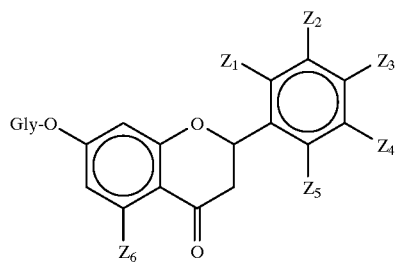

where $Z_1$–$Z_6$ independently of one another are chosen from the group consisting of H, OH, alkoxy and hydroxyalkoxy, where the alkoxy or hydroxyalkoxy groups can be branched or unbranched and may have 1–18 carbon atoms, and where Gly is chosen from the group consisting of mono- and oligoglycoside radicals.

Gly independently of one another is preferably chosen from the group consisting of hexosyl radicals, in particular rhamnosyl radicals and glucosyl radicals. However, if desired, it is also advantageous to use other hexosyl radicals, for example allosyl, altrosyl, galactosyl, gulosyl, idosyl, mannosyl and talosyl. It may also be advantageous according to the invention to use pentosyl radicals.

$Z_1$–$Z_5$ independently of one another are advantageously chosen from the group consisting of H, OH, methoxy, ethoxy and 2-hydroxyethoxy.

Another particularly advantageous flavonoid according to the invention is dihydrorobinetin (3,3',4',5',7-pentahydroxyflavanone). It is characterized by the following structure:

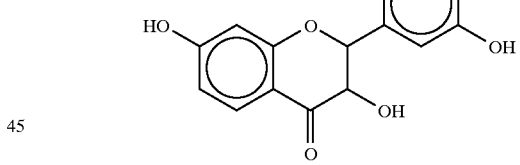

Another particularly advantageous flavonoid according to the invention is taxifolin (3,3',4',5,7-pentahydroxyflavanone). It is characterized by the following structure:

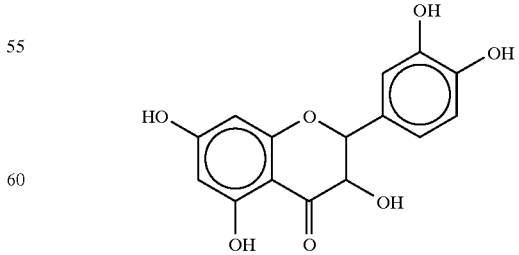

Another particularly advantageous flavonoid according to the invention is eriodictyol-7-glucoside (3',4',5,7-tetrahydroxyflavanone-7-glucoside). It is characterized by the following structure:

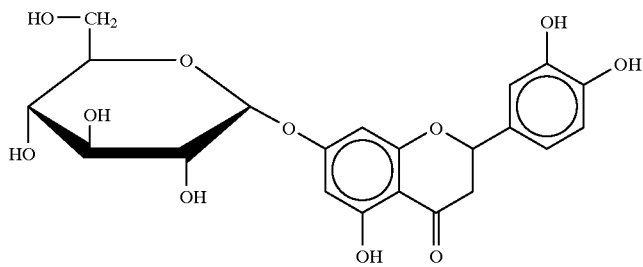

Another particularly advantageous flavonoid according to the invention is flavanomarein (3',4',7,8-tetrahydroxyflavanone-7-glucoside). It is characterized by the following structure:

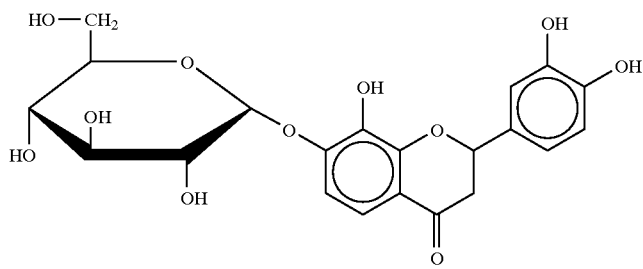

Another particularly advantageous flavonoid according to the invention is isoquercitrin (3,3',4',5,7-pentahydroxyflavanone-3-(β-D-glucopyranoside). It is characterized by the following structural formula:

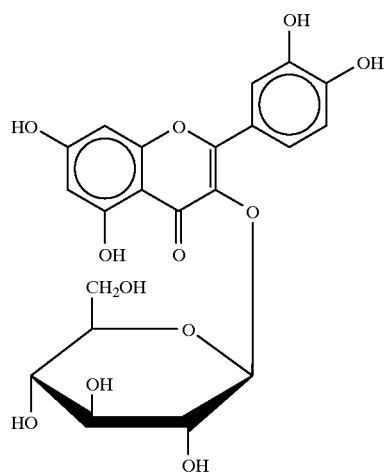

For the purposes of the present invention, it is very particularly preferred to choose the flavone(s) from the group consisting of fisetin, luteolin, quercetin, robinetin, gossypetin and myricetin.

The specification WO 96/18380 describes that flavonoids are suitable for protecting unstable cosmetic active ingredients and additives. It also discloses that corresponding preparations may comprise dibenzoylmethane derivatives, in which case, however, these are intended to exert additional protective effect on the unstable cosmetic active ingredients and additives. In no way could this specification indicate the path to the present invention.

Of the dibenzoylmethane derivatives, the following are used advantageously:

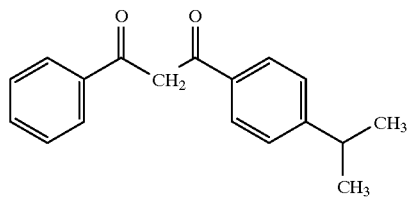

4-Isopropyldibenzoylmethane
CAS No. 63260-25-9

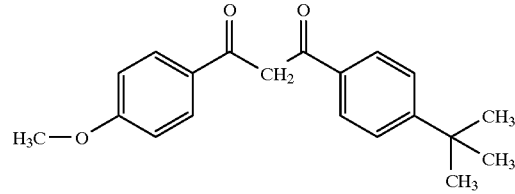

4-(tert-butyl)-4'-Methoxydibenzoylmethane
CAS No. 70356-09-1

In following the teaching according to the invention, light protection formulations are obtainable which have higher stability, in particular stability against decomposition under the effect of light, very particularly UV light, than the prior art would have suggested. In particular, the stability of 4-(tert-butyl)-4'-methoxydibenzoylmethane against decomposition under UV light is drastically increased. It was very particularly surprising that the increase in the stability of dibenzoylmethane, in particular of 4-(tert-butyl)-4'-methoxydibenzoylmethane takes place to the same extent when they are in dissolved form in polar or also non-polar oil components.

The total amount of dibenzoylmethane, in particular 4-(tert-butyl)-4'-methoxydibenzoylmethane in the finished cosmetic or dermatological preparations is advantageously chosen from the range 0.1–10.0% by weight, preferably 0.5–6.0% by weight, based on the total weight of the preparations.

The total amount of flavone derivatives and flavanone derivatives, in particular flavonoids, in the finished cosmetic or dermatological preparations is advantageously chosen from the range 0.1–10.0% by weight, preferably 0.5–6.0% by weight, based on the total weight of the preparations.

It is particularly advantageous to choose the weight ratios of flavone derivatives and flavanone derivatives, in particular flavonoids, to dibenzoylmethanes, to be from 8:1 to 1:5, preferably from 4:1 to 1:2, particularly preferably from 3:1 to 1:1.

Cosmetic and dermatological preparations according to the invention also comprise, although it is not obligatory, inorganic pigments based on metal oxides and/or other metal compounds which are sparingly soluble or insoluble in water, in particular the oxides of titanium ($TiO_2$), zinc (ZnO), iron (for example $Fe_2O_3$), zirconium ($ZrO_2$), silicon ($SiO_2$), manganese (for example MnO), aluminium ($Al_2O_3$) or cerium (for example $Ce_2O_3$), mixed oxides of the corresponding metals and mixtures of such oxides. The pigments are particularly preferably those based on $TiO_2$.

According to the invention, the inorganic pigments are present in hydrophobic form, i.e. they have been surface-treated to repel water. This surface treatment can comprise providing the pigments with a thin hydrophobic layer by processes known per se.

Such a process comprises, for example, producing the hydrophobic surface layer by a reaction according to

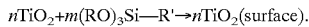

n and m here are stoichiometric parameters to be employed as desired, and R and R' are the desired organic radicals. Hydrophobicized pigments prepared analogously to DE-A 33 14 742, for example, are advantageous.

Advantageous $TiO_2$ pigments are obtainable, for example, under the trade names T 805 from Degussa.

The total amount of inorganic pigments, in particular hydrophobic inorganic micropigments, in the finished cosmetic or dermatological preparations is advantageously chosen from the range 0.1–30% by weight, preferably 0.1–10.0% by weight, in particular 0.5–6.0% by weight, based on the total weight of the preparations.

According to the invention, the cosmetic and/or dermatological light protection formulations can have the customary composition and can be used for cosmetic and/or dermatological light protection, and furthermore for the treatment, care and cleansing of the skin and/or the hair and as a make-up product in decorative cosmetics.

For use, according to the invention, the cosmetic and dermatological preparations are applied to the skin and/or hair in an adequate amount in the manner customary for cosmetics.

Particularly preferred cosmetic and dermatological preparations are those which are in the form of a sunscreen composition. These can advantageously additionally comprise at least one further UVA filter and/or at least one further UVB filter and/or at least one inorganic pigment, preferably an inorganic micropigment.

According to the invention, the cosmetic and dermatological preparations can comprise cosmetic auxiliaries such as are usually used in such preparations, for example preservatives, bactericides, perfumes, antifoams, dyes, pigments which have a colouring action, thickeners, moisturizers and/or humectants, fats, oils, waxes or other customary constituents of a cosmetic or dermatological preparation, such as alcohols, polyols, polymers, foam stabilizers, electrolytes, organic solvents or silicone derivatives.

An additional content of antioxidants is generally preferred. According to the invention, favourable antioxidants which can be used are all antioxidants which are suitable or customary for cosmetic and/or dermatological uses.

The antioxidants are advantageously chosen from the group consisting of amino acids (for example glycine, histidine, tyrosine, tryptophan) and derivatives thereof, imidazoles (for example urocanic acid) and derivatives thereof, peptides such as D,L-camosine, D-camosine, L-camosine and derivatives thereof (for example anserine), carotenoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine sulphoximines, homocysteine sulphoximine, buthionine sulphones, penta-, hexa- and heptathionine sulphoximine) in very low tolerated doses (for example pmol to μmol/kg), and furthermore (metal) chelating agents (for example α-hydroxy-fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoic resin, rutic acid and derivatives thereof, α-glycosylrutin, ferulic acid, furfurylideneglucitol, camosine, butylated hydroxytoluene, butylated hydroxyanisole, nordihydroguaiac resin acid, nor-dihydroguaiaretic acid, trihydroxybutyrophenone, uric acid and derivatives thereof, mannose and derivatives thereof, zinc and derivatives thereof (for example ZnO, $ZnSO_4$), selenium and derivatives thereof (for example selenium methionine), stilbenes and derivatives thereof (for example stilbene oxide, trans-stilbene oxide) and the derivatives of these active ingredients mentioned which are suitable according to the invention (salts, esters, ethers, sugars, nucleotides, nucleosides, peptides and lipids).

The amount of the abovementioned antioxidants (one or more compounds) in the preparations is preferably from 0.001 to 30% by weight, particularly preferably 0.05–20% by weight, in particular 1–10% by weight, based on the total weight of the preparation.

If vitamin E and/or derivatives thereof is or are the antioxidant or antioxidants, it is advantageous to choose the respective concentrations thereof from the range 0.001–10% by weight, based on the total weight of the preparation.

If vitamin A or vitamin A derivatives or carotenes or derivatives thereof is or are the antioxidant or antioxidants, it is advantageous to choose the respective concentrations thereof from the range 0.001–10% by weight, based on the total weight of the preparation.

The lipid phase can advantageously be chosen from the following group of substances:

mineral oils, mineral waxes;

oils, such as triglycerides of capric or of caprylic acid, but preferably castor oil;

fats, waxes and other natural and synthetic fatty substances, preferably esters of fatty acids with alcohols of low C number, for example with isopropanol, propylene glycol or glycerol, or esters of fatty alcohols with alkanoic acids of low C number or with fatty acids;

alkyl benzoates;

silicone oils, such as dimethylpolysiloxanes, diethylpolysiloxanes, diphenylpolysiloxanes and mixed forms thereof.

For the purposes of the present invention, the oil phase of the emulsions, oleogels and hydrodispersions or lipodispersions is advantageously selected from the group consisting of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, from the group consisting of esters of aromatic carboxylic acids and saturated and/or unsaturated, branched and/or unbranched alcohols having a chain length of from 3 to 30 carbon atoms. Such ester oils can then advantageously be selected from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of such esters, e.g. jojoba oil.

The oil phase can also advantageously be selected from the group consisting of branched and unbranched hydrocarbons and hydrocarbon waxes, silicone oils, dialkyl ethers, from the group consisting of saturated or unsaturated, branched or unbranched alcohols, and also fatty acid triglycerides, namely the triglyceryl ester of saturated and/or unsaturated, branched and/or unbranched alkanecarboxylic acids having a chain length of from 8 to 24, in particular 12–18, carbon atoms. The fatty acid triglycerides can advantageously be selected, for example, from the group consisting of synthetic, semi-synthetic and natural oils, e.g. olive oil, sunflower oil, soya oil, peanut oil, rape seed oil, almond oil, palm oil, coconut oil, palm kernel oil and the like.

For the purposes of the present invention, any mixtures of such oil and wax components can also advantageously be used. When required, it may also be advantageous to use waxes, for example cetyl palmitate, as the sole lipid component of the oil phase.

The oil phase is advantageously selected from the group consisting of 2-ethylhexyl isostearate, octyldodecanol, isotridecyl isononanoate, isoeicosane, 2-ethylhexyl cocoate, $C_{12}$–$C_{15}$-alkyl benzoate, caprylic/capric triglyceride and dicaprylyl ether.

Mixtures of $C_{12}$–$C_{15}$-alkyl benzoate and 2-ethylhexyl isostearate, mixtures of $C_{12}$–$C_{15}$-alkyl benzoate and isotridecyl isononanoate and mixtures of $C_{12}$–$C_{15}$-alkyl benzoate, 2-ethylhexyl isostearate and isotridecyl isononanoate are particularly advantageous.

For the purposes of the present invention, of the hydrocarbons, paraffin oil, squalane and squalene can advantageously be used.

The oil phase can advantageously also contain cyclic or linear silicone oils or can consist entirely of such oils, although it is preferable to use an additional content of other oil phase components in addition to the silicone oil or silicone oils.

The silicone oil to be used according to the invention is advantageously cyclomethicone (octamethylcyclotetrasiloxane). However, other silicone oils can advantageously be used for the purposes of the present invention, for example hexamethylcyclotrisiloxane, polydimethylsiloxane, poly(methylphenylsiloxane).

Mixtures of cyclomethicone and isotridecyl isononanoate and mixtures of cyclomethicone and 2-ethylhexyl isostearate are particularly advantageous.

If appropriate, the aqueous phase of the preparations according to the invention advantageously comprises alcohols, diols or polyols of low C number and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols of low C number, for example ethanol, isopropanol, 1,2-propanediol and glycerol, and, in particular, one or more thickeners, which can advantageously be chosen from the group consisting of silicon dioxide, aluminium silicates, polysaccharides and derivatives thereof, for example hyaluronic acid, xanthan gum and hydroxypropylmethylcellulose, particularly advantageously from the group consisting of polyacrylates, preferably a polyacrylate from the group consisting of Carbopols, for example Carbopols of types 980, 981, 1382, 2984 and 5984, in each case individually or in combination.

According to the invention, the cosmetic or dermatological light protection preparations advantageously contain inorganic pigments, in particular micropigments, e.g. in amounts of from 0.1% by weight to 30% by weight, preferably in amounts of from 0.5% by weight to 10% by weight, but especially from 1% by weight to 6% by weight, based on the total weight of the preparations.

It is advantageous according to the invention to employ, in addition to the combinations according to the invention, further oil-soluble UVA filters and/or UVB filters in the lipid phase and/or further water-soluble UVA filters and/or UVB filters in the aqueous phase.

The light protection formulations according to the invention can advantageously comprise further substances which absorb UV radiation in the UVB region, the total amount of filter substances being, for example, from 0.1% by weight to 30% by weight, preferably from 0.5 to 10% by weight, in particular from 1 to 6% by weight, based on the total weight of the preparations, in order to provide cosmetic formulations which protect the skin from the entire region of ultraviolet radiation. They can also be used as sunscreen compositions.

The further UVB filters can be oil-soluble or water-soluble. Advantageous oil-soluble UVB filter substances are, for example:

3-benzylidenecamphor derivatives, preferably 3-(4-methylbenzylidene)camphor and 3-benzylidenecamphor;

4-aminobenzoic acid derivatives, preferably 2-ethylhexyl 4-(dimethylamino)benzoate and amyl 4-(dimethylamino)benzoate;

2,4,6-tris(p-2-ethylhexoxy carbonylanilino)-1,3,5-triazine esters of benzalmalonic acid, preferably di(2-ethylhexyl) 4-methoxybenzalmalonate.

Advantageous water-soluble UVB filter substances are, for example:

salts of 2-phenylbenzimidazole-5-sulphonic acid, such as its sodium, potassium or its triethanolammonium salt, and the sulphonic acid itself;

sulphonic acid derivatives of 3-benzylidenecamphor, such as, for example, 4-(2-oxo-3-bornylidenemethyl)benzenesulphonic acid, 2-methyl-5-(2-oxo-3-bornylidenemethyl)benzenesulphonic acid and salts thereof.

The list of the UVB filters mentioned, which can also be used for the purposes of the present invention, is not of course intended to be limiting.

It may also be advantageous to use UVA filters which have hitherto customarily been present in cosmetic preparations. The amounts used for the UVB combination can be employed.

According to the invention, it may be furthermore advantageous to provide the preparations with further UVA and/or UVB filters, for example certain salicylic acid derivatives, such as

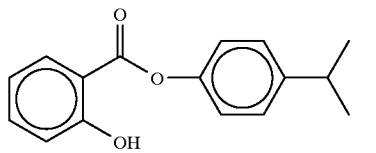

(4-isopropylbenzyl salicylate),

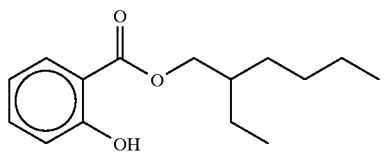

(2-ethylhexyl salicylate, octyl salicylate),

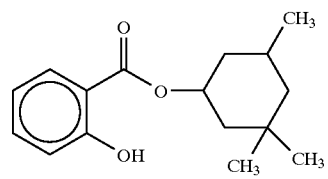

(homomenthyl salicylate).

The total amount of one or more salicylic acid derivatives in the finished cosmetic or dermatological preparations is advantageously chosen from the range 0.1–15.0% by weight, preferably 0.5–8.0% by weight, based on the total weight of the preparations. If ethylhexyl salicylate is chosen, it is advantageous to choose the total amount thereof from the range 0.1–5.0% by weight, preferably 0.5–2.5% by weight. If homomenthyl salicylate is chosen, it is advantageous to choose the total weight thereof from the range 0.1–10.0% by weight, preferably 0.5–5.0% by weight.

Another light protection filter substance which can be used advantageously according to the invention is 2-ethylhexyl 2-cyano-3,3-diphenylacrylate (octocrylene), which is available from BASF under the name UVINUL® N 539 and is characterized by the following structure:

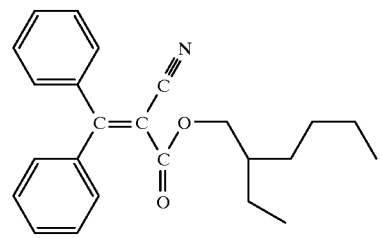

Furthermore, it has proven advantageous for the purposes of the present invention not to use any additional UV filter substances which belong to the group of cinnamic acid derivatives.

The examples below serve to illustrate the present invention without limiting it. Unless stated otherwise, all quantities, proportions and percentages are by weight and based on the total amount or on the total weight of the preparations.

|  | % by weight |
|---|---|
| Example 1 | |
| O/W lotion | |
| | |
| Glyceryl stearate | 3.50 |
| Stearic acid | 1.80 |
| Glycerol | 3.00 |
| Cetylstearyl alcohol | 0.50 |
| Sodium hydroxide (45% strength) | 0.20 |
| Octyldodecanol | 7.00 |
| Dicaprylylether | 8.00 |
| 2,4,6-Tris(p-2-ethylhexoxycarbonylanilino)-1,3,5-triazine | 3.00 |
| Quercetin | 3.00 |
| 4-(tert-butyl)-4'-methoxydibenzoylmethane | 2.00 |
| 2,2-Dimethyl-1,3-propanediol diheptanoate | 6.00 |
| Carbomer | 0.20 |
| Preservative | q.s. |
| Perfume | q.s. |
| Water, demin. | ad 100.00 |
| Example 2 | |
| Hydrodispersion gel | |
| | |
| Pemulen TR-1 | 0.50 |
| Ethanol | 3.50 |
| Glycerol | 3.00 |
| Dimethicone | 1.50 |
| Sodium hydroxide (45% strength) | 0.55 |
| Octyldodecanol | 0.50 |
| Capric/caprylic triglyceride | 5.00 |
| 2,2-Dimethyl-1,3-propanediol diheptanoate | 5.00 |
| Octocrylene | 5.00 |
| Quercetin | 5.00 |
| 4-(tert-Butyl)-4'-methoxydibenzoylmethane | 4.00 |
| Carbomer | 0.20 |
| Preservative | q.s. |
| Perfume | q.s. |
| Water, demin. | ad 100.00 |
| Example 3 | |
| O/W cream | |
| | |
| Glyceryl stearate SE | 3.50 |
| Stearic acid | 3.50 |
| Butylene glycol | 5.00 |
| Cetylstearyl alcohol | 3.00 |
| Sodium hydroxide (45% strength) | 0.35 |
| $C_{12}$—$C_{15}$alkylbenzoate | 10.00 |
| 2,4,6-tris(p-2-ethylhexoxycarbonylanilino)-1,3,5-triazine | 4.00 |
| Quercetin | 5.00 |
| 4-(tert-Butyl)-4'-methoxydibenzoylmethane | 2.00 |
| $TiO_2$ | 3.00 |
| Octyldodecanol | 6.00 |
| Carbomer | 0.20 |
| Preservative | q.s. |

-continued

| | % by weight |
|---|---|
| Perfume | q.s. |
| Water, demin. | ad 100.00 |
| Example 4 | |
| W/O lotion | |
| Polyglyceryl-2-polyhydroxystearate | 3.50 |
| Polyglyceryl-3-diisostearate | 3.50 |
| Butylene glycol | 5.00 |
| Ceresin | 3.00 |
| Sodium hydroxide (45% strength) | 0.35 |
| $C_{12}$—$C_{15}$ alkylbenzoate | 10.00 |
| Quercetin | 2.00 |
| 4-(tert-Butyl)-4'-methoxydibenzoylmethane | 1.00 |
| Eusolex 232 | 2.00 |
| Miglyol 812 | 6.00 |
| Vaseline | 2.00 |
| Preservative | q.s. |
| Perfume | q.s. |
| Water, demin. | ad 100.00 |

We claim:

1. A method of stabilizing a cosmetic or dermatological composition comprising dibenzoylmethane or a derivative thereof which includes the structural formula:

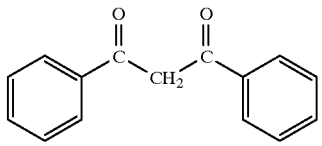

against decomposition of said dibenzoylmethane or derivative thereof caused by UV radiation, said method comprising incorporating into said cosmetic or dermatological composition an amount of a flavone derivative or a flavanone derivative which is effective to stabilize said dibenzoylmethane or derivative thereof against said decomposition.

2. The method according to claim 1, wherein said flavone derivative or flavanone derivative is a flavonoid.

3. The method according to claim 1, wherein said flavone derivative or flavanone derivative is selected from the group consisting of rutin, troxerutin, monoxerutin, dihydrorobinetin, taxifolin, eriodictyol-7-glucoside, quercetin, isoquercitrin, fisetin, luteolin, robinetin, gossypetin and myricetin.

4. The method according to claim 1, wherein said flavone or flavanone derivative is present in said cosmetic or dermatological composition in a concentration of 0.01 to 10% by weight based on the total weight of said cosmetic or dermatological composition.

5. The method according to claim 4, wherein said flavone or flavanone derivative is present in said cosmetic or dermatological composition in a concentration of 0.1 to 5% by weight based on the total weight of said cosmetic or dermatological composition.

6. The method according to claim 5, wherein said flavone or flavanone derivative is present in said cosmetic or dermatological composition in a concentration of 0.2 to 2% by weight based on the total weight of said cosmetic or dermatological composition.

7. The method according to claim 1, wherein said dibenzoylmethane or derivative thereof is selected from the group consisting of 4-isopropyldibenzoylmethane and 4-(tert-butyl)-4'-methoxydibenzoylmethane.

8. The method according to claim 1, wherein said dibenzoylmethane or derivative thereof is present in said cosmetic or dermatological composition in a concentration of 0.1 to 10% by weight based on the total weight of said cosmetic or dermatological composition.

9. The method according to claim 8, wherein said dibenzoylmethane or derivative thereof is present in said cosmetic or dermatological composition in a concentration of 0.5 to 6% by weight based on the total weight of said cosmetic or dermatological composition.

10. The method according to claim 1, wherein the weight ratios of A) said flavone derivative or flavanone derivative to B) said dibenzoylmethane or derivative thereof in said cosmetic or dermatological formulation ranges from 8:1 to 1:5.

11. The method according to claim 10, wherein the weight ratios of A) said flavone derivative or flavanone derivative to B) said dibenzoylmethane or derivative thereof in said cosmetic or dermatological formulation ranges from 4:1 to 1:2.

12. The method according to claim 11, wherein the weight ratios of A) said flavone derivative or flavanone derivative to B) said dibenzoylmethane or derivative thereof in said cosmetic or dermatological formulation ranges from 3:1 to 1:1.

* * * * *